(12) United States Patent
Balagurusamy et al.

(10) Patent No.: US 9,869,658 B2
(45) Date of Patent: Jan. 16, 2018

(54) ELECTRONIC LABEL FREE DETECTION OF DNA COMPLEXES USING NANOGAP

(71) Applicant: International Business Machines Corporation, Armonk, NY (US)

(72) Inventors: Venkat K. Balagurusamy, Suffern, NY (US); Stanislav Polonsky, Putnam Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 368 days.

(21) Appl. No.: 14/337,401

(22) Filed: Jul. 22, 2014

(65) Prior Publication Data
US 2016/0024567 A1 Jan. 28, 2016

(51) Int. Cl.
| | |
|---|---|
| G01F 1/64 | (2006.01) |
| G01L 1/20 | (2006.01) |
| G01L 9/18 | (2006.01) |
| G01N 27/447 | (2006.01) |
| G01N 33/487 | (2006.01) |
| C12Q 1/68 | (2006.01) |

(52) U.S. Cl.
CPC ..... *G01N 27/44791* (2013.01); *C12Q 1/6816* (2013.01); *G01N 33/48721* (2013.01)

(58) Field of Classification Search
CPC ............................................. G01N 33/48721
See application file for complete search history.

(56) References Cited

U.S. PATENT DOCUMENTS

| | | | |
|---|---|---|---|
| 6,905,586 B2 | 6/2005 | Lee et al. | |
| 7,279,337 B2 | 10/2007 | Zhu | |
| 8,062,596 B2 | 11/2011 | Yun et al. | |
| 8,262,879 B2 | 9/2012 | Oliver | |
| 8,283,936 B2 | 10/2012 | Iqbal et al. | |

(Continued)

FOREIGN PATENT DOCUMENTS

| | | |
|---|---|---|
| JP | 2005249753 A | 9/2005 |
| JP | 2013519074 A | 5/2013 |

(Continued)

OTHER PUBLICATIONS

Detection of Local Protein Structures along DNA Using Solid-State Nanopores Stefan W. Kowalczyk, Adam R. Hall, and Cees Dekker Nano Letters 2010 10 (1), 324-328.*

(Continued)

*Primary Examiner* — Ibrahime A Abraham
(74) *Attorney, Agent, or Firm* — Cantor Colburn LLP; Vazken Alexanian

(57) ABSTRACT

A technique for electrical detection of a molecule is provided. A fluidic bridge is formed between a nanopipette and a fluid cell, where the molecule is in the nanopipette. A voltage difference is applied between the nanopipette and the fluid cell, where the fluid cell contains an electrolyte solution. Entry of the molecule into the fluidic bridge is determined by detecting a fore pulse. The fluidic bridge between the nanopipette and the fluid cell is broken to form a nanogap. In response to waiting a time interval, the fluidic bridge is reformed between the nanopipette and the fluid cell to close the nanogap. The molecule is determined to exit the nanopipette by detecting an after pulse.

13 Claims, 8 Drawing Sheets

(56) References Cited

U.S. PATENT DOCUMENTS

| | | | |
|---|---|---|---|
| 8,492,714 B2 | 7/2013 | Reed et al. | |
| 2004/0241681 A1* | 12/2004 | Korchev | B01J 19/0046 |
| | | | 506/39 |
| 2010/0184062 A1 | 7/2010 | Steinmuller-Nethl et al. | |
| 2011/0236980 A1 | 9/2011 | Rea | |
| 2012/0288948 A1 | 11/2012 | Lindsay et al. | |
| 2012/0326732 A1 | 12/2012 | Cho et al. | |
| 2013/0043131 A1* | 2/2013 | Balagurusamy | G01N 33/48721 |
| | | | 204/452 |

FOREIGN PATENT DOCUMENTS

| | | |
|---|---|---|
| WO | WO2013016486 A1 | 1/2013 |
| WO | WO02013046116 A1 | 4/2013 |

OTHER PUBLICATIONS

Stanislav Polonsky and Venkat S. K. Balagurusamy, Phenomenological theory of a charged polymer molecule in a nanosized gap between two fluidic reservoirs, 2013 EPL 103 68007, 1-4.*

Shizhi Qian and Ye Ai, Electrokinetic Particle Transport in Micro-/Nanofluidics: Direct Numerica, CRC Press; 1 edition (Jun. 19, 2012), p. 308.*

W. Lee, et al., "Nanochemical Protein Concentration Detector Using a Nanogap Squeezing Actuator with Compensated Displacement Monitoring Electrodes," Journal of Microelectromechanical Systems, vol. 16, No. 4, Aug. 2007; pp. 802-808.

* cited by examiner

US 9,869,658 B2

1

ELECTRONIC LABEL FREE DETECTION OF DNA COMPLEXES USING NANOGAP

BACKGROUND

Embodiments relate to detection of molecules, and more particularly to detection of molecules (e.g., DNA, RNA, etc.) via a controllable nanogap.

Nanopore sequencing is a method for determining the order in which nucleotides occur on a strand of deoxyribonucleic acid (DNA). A nanopore is a small hole on the order of several nanometers in internal diameter. The theory behind nanopore sequencing relates to what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be placed around the nanopore so that DNA bases can be differentiated while the DNA passes through the nanopore.

DNA could be driven through the nanopore by using various methods. For example, an electric field might attract the DNA towards the nanopore, and DNA might eventually pass through the nanopore.

BRIEF SUMMARY

According to an embodiment, a method for electrical detection of a molecule is provided. The method includes forming a fluidic bridge between a nanopipette and a fluid cell, where the molecule is in the nanopipette, and applying a voltage difference between the nanopipette and the fluid cell, where the fluid cell contains an electrolyte solution. The method includes determining entry of the molecule into the fluidic bridge by detecting a fore pulse, breaking the fluidic bridge between the nanopipette and the fluid cell to form a nanogap, in response to waiting a time interval, reforming the fluidic bridge between the nanopipette and the fluid cell to close the nanogap, and determining that the molecule exits the nanopipette by detecting an after pulse.

According to an embodiment, a system for electrical detection of a molecule is provided. The system includes a nanopipette filled with an electrolyte solution, a fluid cell filled with the electrolyte solution, a nanopositioner attached to the nanopipette in order to move the nanopipette with respect to the fluid cell, and a control system connected to the nanopositioner in order to control movement of the nanopipette. The control system is configured to perform operations comprising forming a fluidic bridge between the nanopipette and the fluid cell, where the molecule is in the nanopipette, applying a voltage difference between the nanopipette and the fluid cell, and determining entry of the molecule into the fluidic bridge by detecting a fore pulse. Also, the control system is configured to break the fluidic bridge between the nanopipette and the fluid cell to form a nanogap in response to waiting a time interval, reform the fluidic bridge between the nanopipette and the fluid cell to close the nanogap, and determine that the molecule exits the nanopipette by detecting an after pulse.

According to an embodiment, a method for electrical detection of binding of a protein to a molecule is provided. The method includes forming a fluidic bridge between a nanopipette and a fluid cell, where the molecule and the protein are in the nanopipette, applying a voltage difference between the nanopipette and the fluid cell, where the fluid cell contains an electrolyte solution, determining entry of the molecule into the fluidic bridge by detecting a fore pulse, and breaking the fluidic bridge between the nanopipette and the fluid cell to form a nanogap. The method includes in response to waiting a time interval, reforming the fluidic bridge between the nanopipette and the fluid cell to close the nanogap, and determining that the protein is bound to the molecule by detecting an after pulse when the molecule exits the nanopipette.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

DETAILED DESCRIPTION

Embodiments provide a technique for manipulating a segment of a charged macromolecule (molecules include DNA, RNA, protein, etc.) inside a transient nanogap between two fluidic reservoirs. The nanogap is transient because the nanogap can be created and closed as desired. This technique may use an FPGA-driven nanopositioner (i.e., z stage) to control the coupling of a nanopipette with the liquid surface of a fluidic cell. The developed platform enables testing of predictions for the behavior of charged macromolecule in a nanogap between two fluidic reservoirs, without fabricating nanochannels/nanopores.

Figure 1:
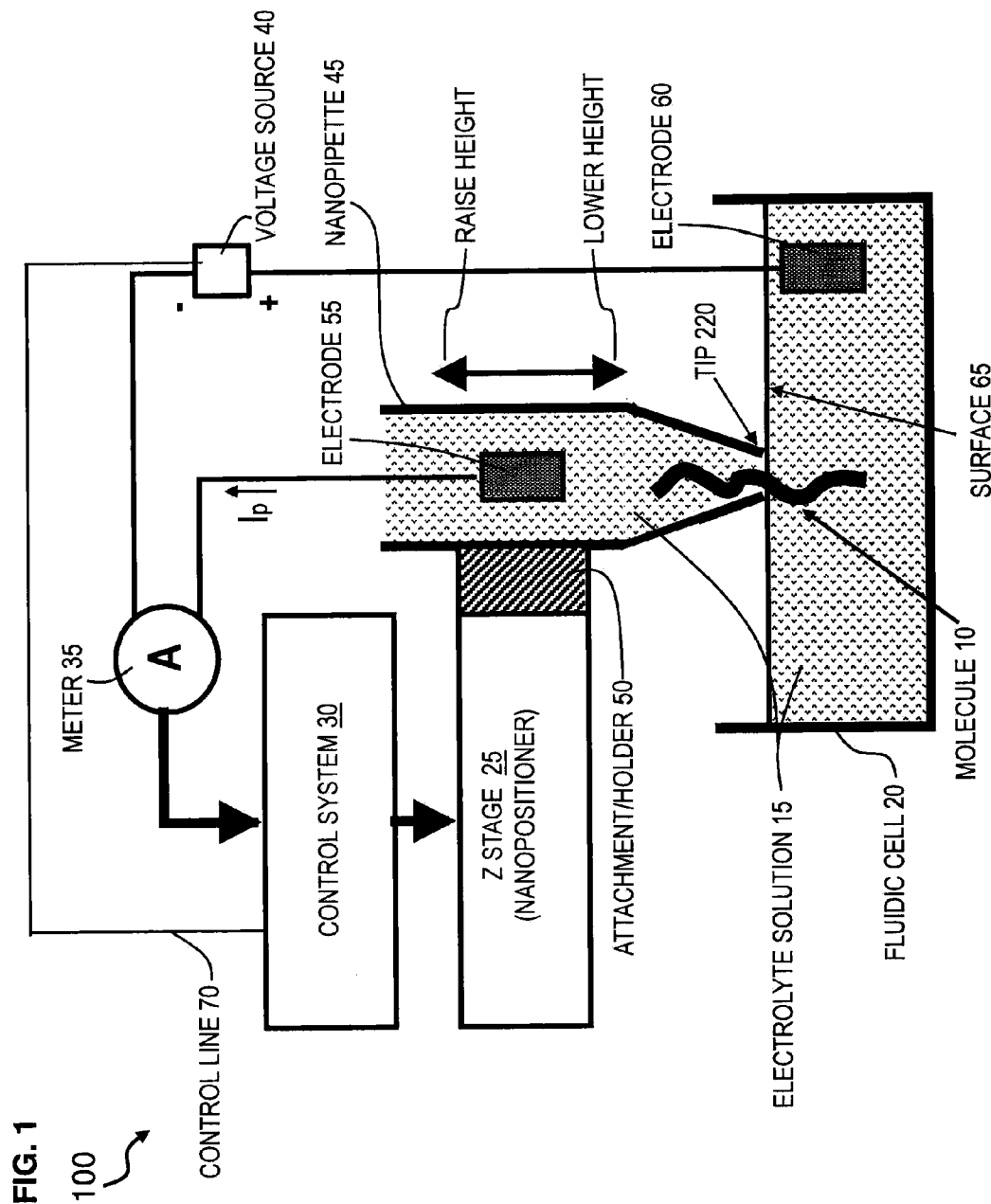
FIG. 1 illustrates a schematic of an example test setup utilizing a pipette according to an embodiment.

FIG. 1 illustrates a schematic of an experimental (test) setup 100 which utilizes a nanopipette 45 as a single molecule detector according to an embodiment. FIG. 1 shows a fluidic cell 20 and nanopipette 45 filled with a buffered electrolyte solution 15. The nanopipette 45 includes an electrode 55 in the buffered electrolyte solution 15, and the fluidic cell 20 includes an electrode 60 in the buffered electrolyte solution 15. The electrodes 55 and 60 are connected to a voltage source 40 to provide voltage (a voltage bias) to the electrodes 55 and 60. In one case, the electrodes 55 and 60 may be made of Ag and/or AgCl. In one case, the electrolyte solution 15 may include 1 mole (M) KCl at a pH 8.0. A meter 35 is connected in the circuit to measure ionic current (and/or voltage, etc.). A z stage 25 (which is a nanopositioner) is connected to the nanopipette 45 via an attachment 50 such as a holder or clamp (as understood by one skilled in the art). The clamp extends from the Z stage 25 nanopositioner to move up and down as moved by the nanopositioner. The nanopipette 45 is physically attached to the attachment 50 holder. The z stage 25 is configured to raise and lower the nanopipette 45 (in nanometer (nm) increments) to contact the surface 65 of the buffered electrolyte solution 15 in the fluidic cell 20. Optionally, a control system 30 may be utilized to raise and lower the nanopipette 45 in and out of the buffered electrolyte solution 15 of the fluidic cell 20.

The nanopipette 45 is a long tapered capillary, and unlike a nanopore/nanochannel, the nanopipette 45 does not need a thin high-capacitance membrane for support. As a result, the nanopipette 45 has a very low parasitic capacitance, which allows fast and low-noise ionic current measurements (via the meter 35 and voltage source 40). In one case, the experimenters used a Sutter P-2000 laser puller to make nanopipettes from Sutter QF100-70 quartz capillaries with an outer diameter (OD)=1 millimeter (mm) and an inner diameter (ID)=0.7 mm. The capillaries used had a filament to make filling the pipette with the electrolyte solution easier. The pipettes can be made using a two-line puller program.

As noted above, the nanopipette 45 filled with the buffered electrolyte solution 15 containing dsDNA molecule 10 is mounted on an electronically controlled z-stage 25. The ionic current established through the nanopipette 45 on the application of a bias voltage (via the voltage source 40) is used to detect the passage of DNA molecules 10 through nanopipette 45. By raising the nanopipette 45 soon after the detection of the DNA molecule entry (via measured ionic current by the meter 35) into the fluidic cell 20, a transient nanogap 250 (shown in FIG. 2) can be created. After the creation of the nanogap 250 the nanopipette 45 is lowered to reestablish contact with the electrolyte solution 15, the meter 35 monitors the ionic current through the nanopipette 45 which enables the detection of the escape of the DNA molecule 10 trapped in the nanogap 250. The details of setup 100 including the control system 30 and the protocols are described further herein. Note that the control system 30, meter 35, and voltage source 40 may be implemented in computer system 800 in FIG. 8. The computer system 800 may also control the z stage 25 nanopositioner in the manner discussed herein.

Figure 2:
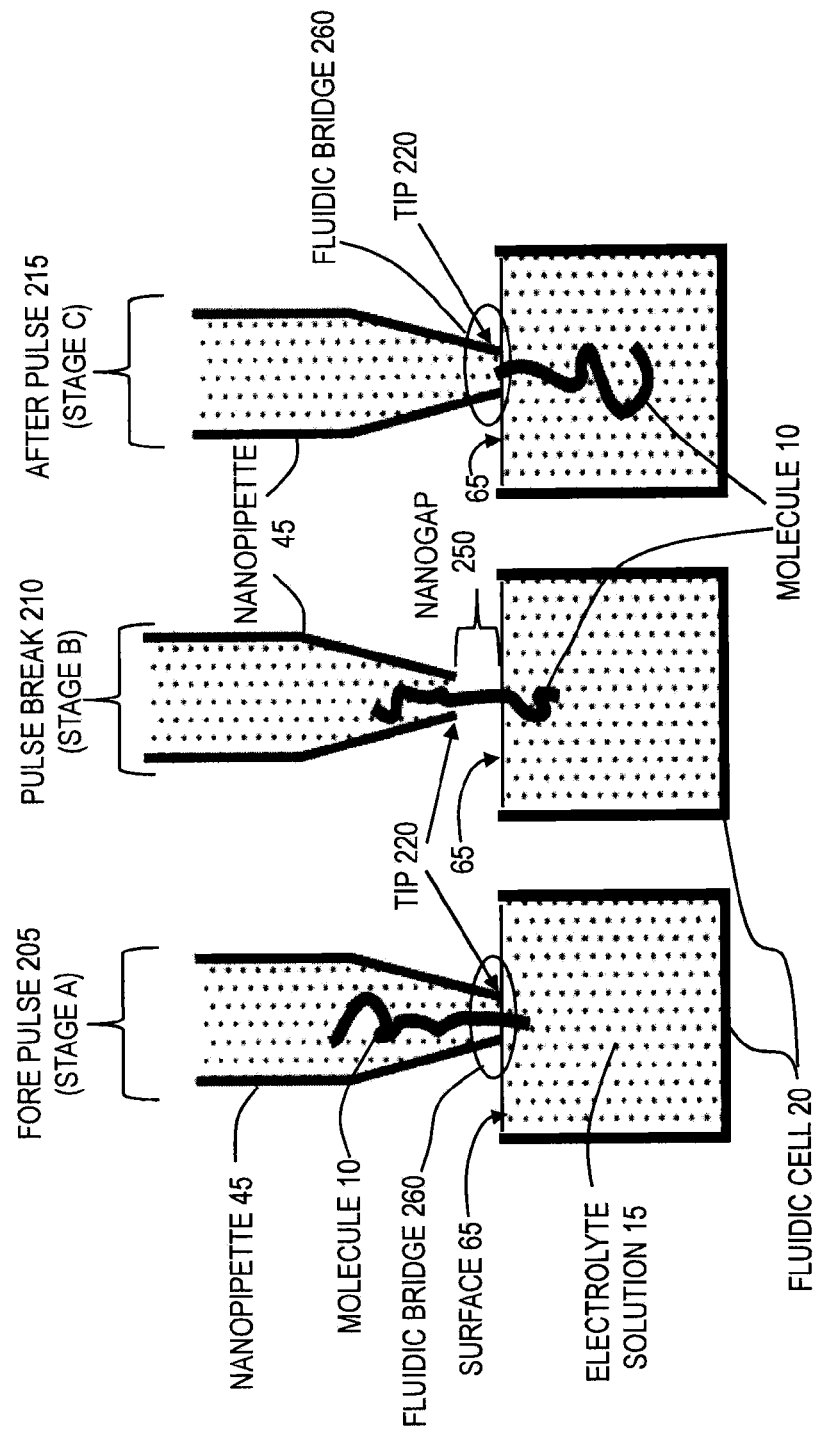
FIG. 2 illustrates the dynamics of nanogap creation by moving the pipette, along with detection of the translocation of the molecule according to an embodiment.
Figure 3:
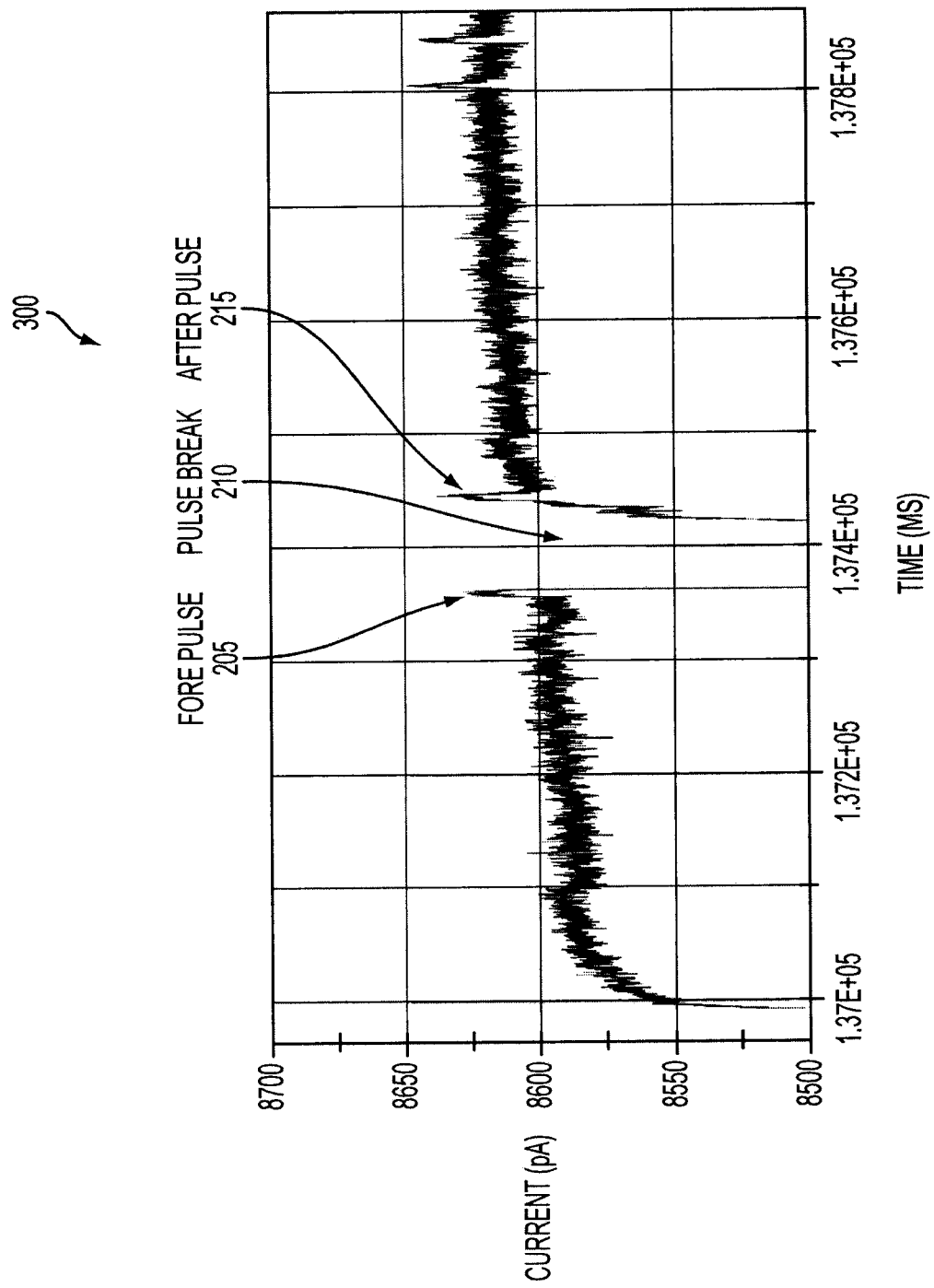
FIG. 3 illustrates a graph of ionic current pulses related to translocation of the molecule during stages of operation according to an embodiment.

FIG. 2 illustrates the dynamics of nanogap 250 creation by moving (raising and lowering) the nanopipette 45 and detection of the translocation of the molecule 10 in the nanopipette 45 according to an embodiment. Although some elements are omitted for the sake of clarity, FIG. 2 includes all of the elements of FIG. 1. FIG. 2 illustrates stages of operation related to the detection of an ionic current pulses or no ionic current pulse. FIG. 3 illustrates a graph 300 of ionic current pulses related to translocation of the molecule 10 during the stages of operation (including the vertical movement of the nanopipette 45) according to an embodiment. The operations/actions of FIG. 2 (along with FIGS. 1 and 3-8) may be caused by, initiated by, stopped by, and/or controlled by the control system 30 based on feedback (the ionic current measured by the meter 35) from the meter 35 and/or voltage source 40.

In FIG. 2, stage A shows when the z stage 25 nanopositioner has brought (lowered) the tip 220 of the nanopipette 45 into physical contact with the surface 65 of the electrolyte solution 15 contained in the fluidic cell 20 so as to form a fluidic bridge 220. In stage A, the voltage source 40 is turned on to generate a voltage bias (voltage) via the electrode 55 in the nanopipette 45 and the electrode 60 in the fluidic cell 20. During stage A, the tip 220 of the nanopipette 45 filled with electrolyte solution 15 completes the circuit with the electrolyte solution 15 in the fluidic cell 20 such that ionic current is now flowing, and the meter 35 measures ionic current. The fluidic bridge 260 is the completed circuit formed by the electrolyte solution 15 in the nanopipette 45 being in electrical connection with the electrolyte solution 15 in the fluidic cell 20. During stage A, the voltage bias causes a first part of the molecule 10 to exit the tip 220 and then translocate (move) into the electrolyte solution 15 contained in the fluidic cell 20, while the other part of the molecule 10 (simultaneously) remains in the tip of the nanopipette 45. At the time of translocation, the meter 35 measures a fore pulse 205 shown in FIG. 3, and the fore pulse 205 is a spike in the ionic current indicative of the first part of the molecule 10 exiting the tip 220 and moving into the electrolyte solution 15 in the fluidic cell 20.

Figure 4:
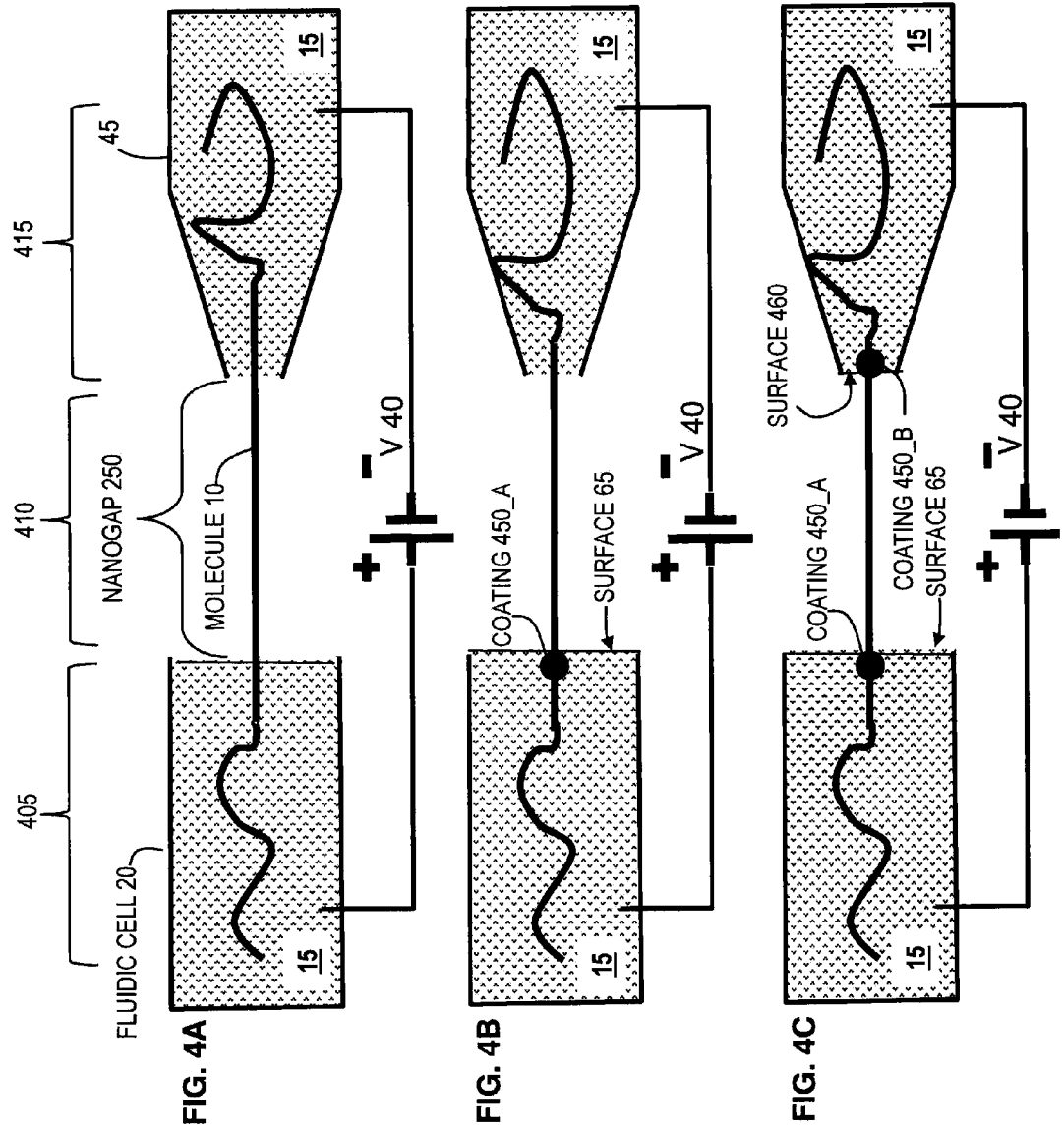
FIG. 4A illustrates a molecule with no attached coating in the nanogap according to an embodiment.
FIG. 4B illustrates the molecule with a coating attached in the nanogap according to an embodiment.
FIG. 4C illustrates a coating attached at two segments of the molecule according to an embodiment.

In FIG. 2, stage B shows when the z stage 25 nanopositioner has raised (lifted) the tip 220 of the nanopipette 45 out of physical contact with the surface 65 of the electrolyte solution 15 so as to break the fluidic bridge 220 and form a nanogap 250. The nanogap 250 is the separation of distance between the surface 65 of the electrolyte solution 15 in the fluidic cell 20 and the tip 220 of the nanopipette 45. In stage B in FIG. 2, the meter 35 measures a pulse break 210 in the ionic current shown in FIG. 3. The pulse break 210 is a drop in the ionic current that is recognized by the meter 35. This pulse break 210 occurring immediately after the fore pulse 205 confirms the creation of nanogap 250. During stage B, the ionic current does not have a complete path to flow once the nanogap 250 is opened. In one case, the nanogap 250 may be less than 500 nanometers (nm). The nanogap 250 may be 10, 20, 30, 40, 50, 60 . . . 100, 150 nanometers to about 500 nanometers. During stage B, there may be three sections of the molecule 10 as shown in FIGS. 4A, 4B, and 4C (generally referred to as FIG. 4). By reapplying the voltage bias (via voltage source 40), the first part 405 of the molecule 10 exits the tip 220 and is in the electrolyte solution 15 of the fluidic cell 20; the exiting of the first part 405 of the molecule 10 is determined/confirmed by detecting the fore pulse 205. A second/middle part 410 of the molecule 10 is now in the nanogap 250 (i.e., the part 410 is neither in the tip 220 nor in the electrolyte solution 15 contained in the fluidic cell 20). A third/end part 415 of the molecule 10 is still in the (tip 220 of the) nanopipette 45. Note that in one case a lower amount of voltage may still be turned on during stage B. In another case, the voltage of voltage source 40 is turned off (i.e., 0 volts).

In FIG. 2, stage C shows when the z stage 25 nanopositioner has brought (lowered) the tip 220 of the nanopipette 45 back into physical contact with the surface 65 of the electrolyte solution 15 contained in the fluidic cell 20 so as to restore the fluidic bridge 220. The circuit is completed again, and the voltage source 40 is turned on (and/or increased) to generate the voltage bias again via the electrode 55 in the nanopipette 45 and the electrode 60 in the fluidic cell 20. During stage C, the meter 35 measures an after pulse 215 shown in FIG. 3, and the after pulse 215 is a spike in the ionic current indicative of the third/end part 415 of the molecule 10 exiting tip 220 of the nanopipette 45 to completely reside in the electrolyte solution 15 in the fluidic cell 20. The after pulse 215 also confirms that the third/end part 415 of the molecule 10 was actually in the nanopipette 45 during stage B.

Now, turning to FIGS. 4A, 4B, and 4C (generally referred to as FIG. 4), FIG. 4 illustrates further details of manipulating the molecule 10 while the nanogap 250 is formed according to an embodiment. As noted above, FIG. 4 shows the first part 405 of the molecule 10 in the fluidic cell 20, the second/middle part 410 in the nanogap 250, and the end part 415 in the nanopipette 45. FIG. 4 corresponds to stage B in FIG. 2, when the nanogap 250 is present.

In FIG. 4A, the molecule is a (pure) dsDNA (double strand DNA) molecule with no coating. In FIG. 4A, the dsDNA molecule 10 is not trapped. The nanogap 250 is transparent to the pure dsDNA (i.e., with no coating).

In FIG. 4B, the molecule 10 is a dsDNA molecule with a coating 450_A attached. The coating 450_A (and coating 450_B discussed below in FIG. 4C) are DNA-binding molecules with a high charge contrast. On the other hand, the pure dsDNA molecule (with no attached coating 450A and/or 450_B) has a low charge contrast. Empirically, charge contrast can be defined as the ratio of the charge per unit length of bare DNA molecule over the same length of the molecule coated with certain molecules that bind to the DNA, examples being RecA and TALE proteins. The coating 450_A and coating 450_B may be a protein. Other examples of the coating 450_A and coating 450_B include RecA and TALE proteins (further example proteins can be found in the following which are herein incorporated by reference: S. W. Kowalczyk, A. R. Hall, and C. Dekker, "*Detection of Local Protein Structures along DNA Using Solid-State Nanopores*" Nano Lett. 10, 324 (2009); F. Zhang, L. Cong, S. Lodato, S. Kosuri, G. M. Church and P. Arlotta, "*Efficient construction of sequence-specific TAL effectors for modulating mammalian transcription*", Nature Biotechnology, 29, 149-153 (2011)). In FIG. 4B, the coating 450_A is applied to one segment of the dsDNA molecule 10. In this case, the coating 450_A is applied/attached to the first part 405 of the molecule 10 in order to trap the molecule 10 in the nanogap 250. The coating 450_A has a high contrast ratio which binds coating 450_A at/to the top surface 65 of the electrolyte solution 15 in the fluidic cell 20. Consequently, the first part 405 of the molecule 10 is bound to the surface 65 of the electrolyte solution 15 such that the molecule 10 is trapped in place. When the molecule 10 is trapped in the nanogap 250 via the coating 450_A, it is assumed that the voltage bias (voltage) of the voltage source 40 is turned off and/or is lower than the voltage bias applied to drive the molecule 10 into the fluidic cell in stages A and C. Having a low voltage or no voltage applied in FIG. 4B ensures that the voltage of the voltage source 40 does not drive the molecule 10 completely in the fluidic cell 20 and out of the nanopipette 45.

FIG. 4C is similar to FIG. 4B, but FIG. 4C shows a second coating 450_B attached on the end (third) part 415 of the molecule 10. The second coating 450_B is applied to the last segment of the dsDNA molecule 10 in order to trap the molecule 10 in the nanogap 250. The coating 450_B has a high charge contrast ratio which binds coating 450_B at/to the surface 460 of the electrolyte solution 15 in tip 220 of the nanopipette 45. Consequently, the end part 415 of the molecule 10 is bound to the surface 460 of the electrolyte solution 15 (in the nanopipette 45) such that the molecule 10 is trapped in place. When the molecule 10 is trapped in the nanogap 250 via the coating 450_B, it is (again) assumed that the voltage bias (voltage) of the voltage source 40 is turned off and/or lower than the voltage bias applied to drive the molecule 10 into the fluidic cell in stages A and C. In one case only the coating 450_A may be utilized to trap the molecule in the nanogap 250. In another case, only the coating 450_B may be utilized to trap the molecule 10 in the nanogap 250.

In another case, both coatings 450A and 450_B may be utilized to trap the molecule 10. Further, when both coatings 450_A and 450B are utilized, the middle part 410 of the molecule 10 can be stretched. In one case, when the separation between the coatings 450_A and 450_B are approximately equal to the distance/width of the nanogap 250, the middle part 410 of the molecule 10 is stretched/extended. In one case, the z stage 25 nanopositioner can be incrementally moved upward in order to widen the nanogap 250 (to a predetermined distance that separates the coatings 450_A and 450B) in order to stretch the middle part 410 of the molecule 10 all while the coating 450_A binds to the surface 65 and while the coating 450_B binds to the surface 460. In one case, the voltage of voltage source 40 may be applied at a predefined magnitude/level less than the voltage required to break the coating to surface bond between the coating 450_A and surface 65 and/or less than the coating to surface bond between the coating 450_B and surface 460.

Note that the coating 450_A and coating 450_B may be generally referred to as coating molecules 450. Prior to binding with the molecule 10, the coating molecules 450 may be placed in the nanopipette 45 such that the coating molecules 450 are initially unattached to the molecule 10, which for testing to determine if the coating molecules 450 are candidates to bind with the molecule 10. The binding of the coating molecule 450 with the molecule 10 can be utilized to determine that the particular coating molecule 450 being tested (which can be a protein) is a transcription factor. The binding of the coating molecule 450 can be determined by utilizing the test setup 100 in at least two ways. In the first case, anytime the molecule 10 is trapped in the nanogap 250, the control system 30 can determine that the particular coating molecule 450 being tested has bound to the molecule 10 because the unbound molecule 10 does not get trapped in the nanogap 250. In the second case, the control system 30 can determine that detection of the after pulse 216 (measured by the meter 35) is a result of the coating molecule 450 having successfully bound to the molecule 10, and this after pulse 215 is detected when the bound coating molecule 450 and molecule 10 complex exit the nanopipette 45. In one case, to discriminate/distinguish (the after pulse 215) when the unbound molecule 10 exits the nanopipette 45 and when the bound molecule 10 (i.e., bound to the coating molecule 450) exits the nanopipette 45, a baseline magnitude for the unbound molecule 10 (e.g., pure DNA) is established. The baseline magnitude for the unbound molecule 10 is lower than the magnitude of the after pulse 215 created by the bound molecule 10 (i.e., bound to coating molecule 450). Therefore, when the meter 35 detects the magnitude of the after pulse 215 greater than the baseline magnitude (with unbound molecule 10, such as pure DNA) for the after pulse 215, the control system 30 (computer system 800 discussed herein) determines that the coating molecule 450 has successfully bound to the molecule 10.

Figure 5:
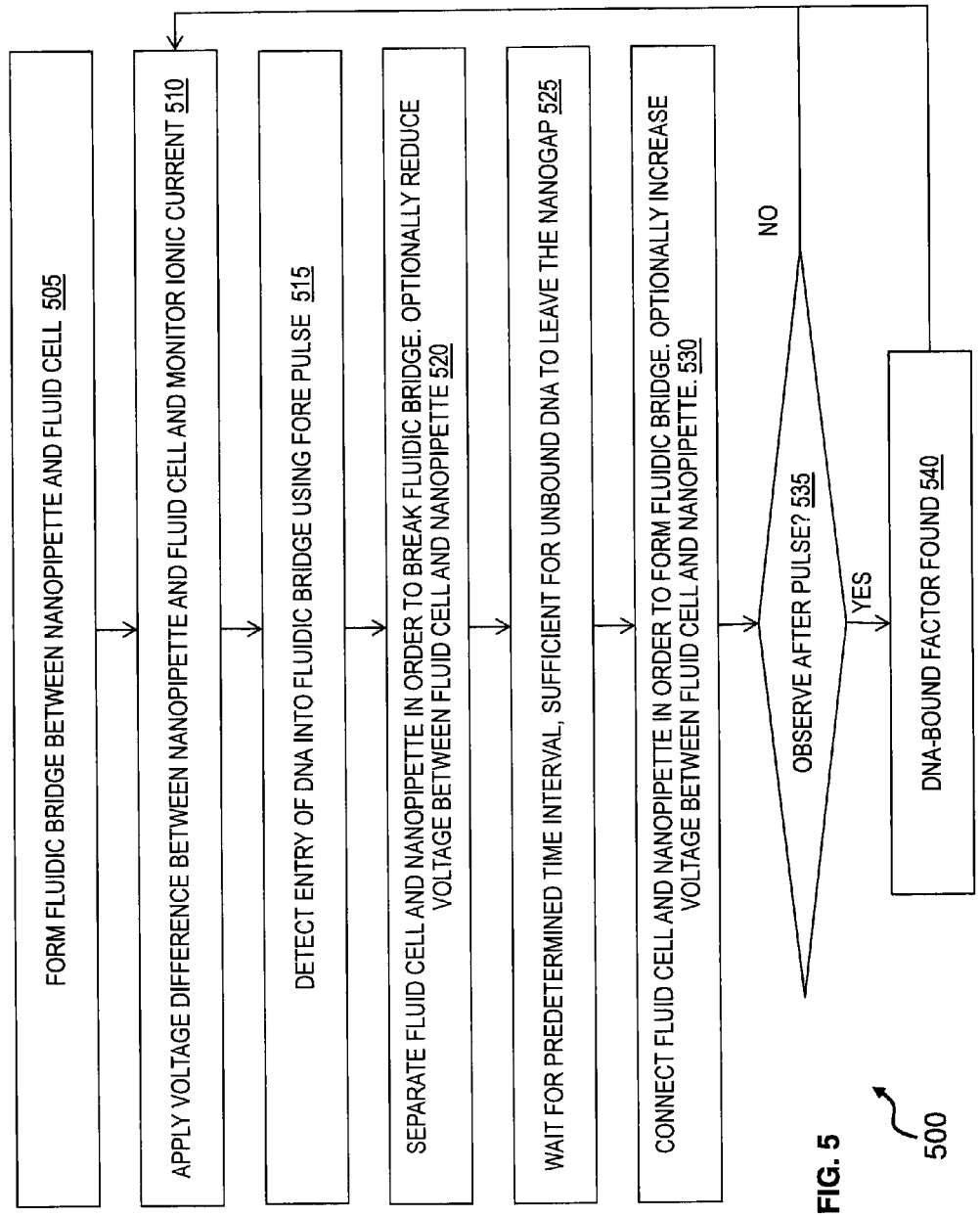
FIG. 5 is a flow chart illustrating manipulation of the molecule and detection of binding factor complexes according to an embodiment.

FIG. 5 is a flow chart 500 illustrating manipulation of the molecule 10 and detection of binding factor complexes (i.e., the coating molecule 450 bound to the molecule 10) according to an embodiment. The coating molecules 450 being tested for binding are deposited into the nanopipette 45 along with the molecule 10 as understood by one skilled in the art. When a particular type of coating molecule 450 (e.g., protein) binds to the molecule 10, this coating molecule 450 is determined to be a DNA-bound factor. The various operations in FIG. 5 may be controlled by, initiated by, determined by, and/or caused by control system 30 (which may be implemented in the computer 800).

As understood by one skilled in the art, DNA-binding proteins are proteins that are composed of DNA-binding domains and thus have a specific or general affinity for either single or double stranded DNA. DNA-binding proteins include transcription factors which modulate the process of transcription, various polymerases, nucleases which cleave DNA molecules, and histones which are involved in chromosome packaging and transcription in the cell nucleus. A transcription factor (sometimes called a sequence-specific DNA-binding factor) is a protein that binds to specific DNA sequences, thereby controlling the flow (or transcription) of genetic information from DNA to messenger RNA. The coating molecules 450 may be tested for their use as DNA-binding proteins using the test setup 100 according to embodiments.

At block 505, the fluidic bridge 260 is formed between the nanopipette 45 and the fluidic cell 20 as shown in stage A in FIG. 2.

At block 510, the voltage source 40 applies a voltage difference (i.e., voltage) between the nanopipette 45 and fluidic cell 20, while monitoring the ionic current via the meter 35.

At block 515, the meter 35 is configured to detect entry of the molecule 10 into the fluidic bridge 260 using the fore pulse 515.

At block 520, the z stage 25 (nanopositioner) forms the nanogap 250 by separating the fluidic cell 20 and nanopipette 45 in order to break the fluidic bridge 260. Optionally, the voltage (of the voltage source 40) is reduced between fluidic cell 20 and nanopipette 45.

At block 525, the control system 30 (which may be implemented in computer 800) is configured to wait for a predetermined time interval, sufficient for an unbound molecule (DNA) to leave the nanogap 250 in the event that the coating molecule 450 did not bind to the molecule 10, before causing Z stage 25 to lower back into physical contact with the electrolyte solution in the fluidic cell 20. This predetermined time interval may be at least 5, 10, 15, 20 milliseconds (ms).

At block 530, the control system 30 controls the z stage 25 to reconnect the fluidic cell 20 and nanopipette 45 in order to reform the fluidic bridge 260. The voltage source 40 increases the voltage between the fluidic cell 20 and nanopipette 45. The control system 30 (e.g., computer 800) waits a predetermined time interval (at least 5, 10, 15, 20 . . . 30 ms) to determine if the meter 35 detects the after pulse 215 at decision block 535 (as shown in stage C).

When the meter 35 does not measure the after pulse 215 (with the large magnitude indicative of the bound complex comprising the molecule 10 bound to the coating molecule 450), the flow proceeds back to block 510 so that another molecule can move to the tip 220 (as in stage A). When the meter 35 does measure the after pulse 215 (with the large magnitude indicative of the bound complex comprising the molecule 10 bound to the coating molecule 450), the computer 800 (control system 30) and/or experimenter/operator determines that that the DNA bound factor is found at block 540. In other words, the computer 800 (control system 30) and/or operator determines that the coating molecule 450 has bound to the molecule 10. The control system 30 may include one or more processors that execute computer executable instructions, and the control system 30 is configured to control the movement of the z stage 25 in order to move the nanopipette as discussed herein. The control system 30 is configured to control the level of voltage applied by the voltage source 40 and to turn the voltage source 40 on/off via control line 70, as discussed herein. Different levels/magnitudes of ionic current measured by the meter 35 operate as triggers to cause the control system 30 to move the nanopipette 45 (via z stage 25) up or down and/or to increase/decrease the voltage (via voltage source 40). The control system 30 is configured to detect/determine the movement and location of the molecule 10 according to measured ionic levels (i.e., spikes and no spikes).

Also, the control system 30 is configured to detect/determine the binding of the coating molecule 450 to the molecule 10 based on the measured ionic level. In one test setting, the presence of the after pulse 215 indicates that the coating molecule 450 has bound to the molecule 450. The control system 30 (computer 800) is configured to determine that the protein (e.g., coating molecule 450) is not bound to the molecule 10 by detecting no after pulse 215 after the nanogap 250 has be closed to reform the fluidic bridge 260 and/or by detecting the after pulse 215 with a baseline magnitude corresponding to the molecule 10 being unbound; the after pulse baseline magnitude (for unbound molecule 10) is lower than an after pulse magnitude corresponding to the protein (coating molecule 450) bound to the molecule 10.

Figure 6:
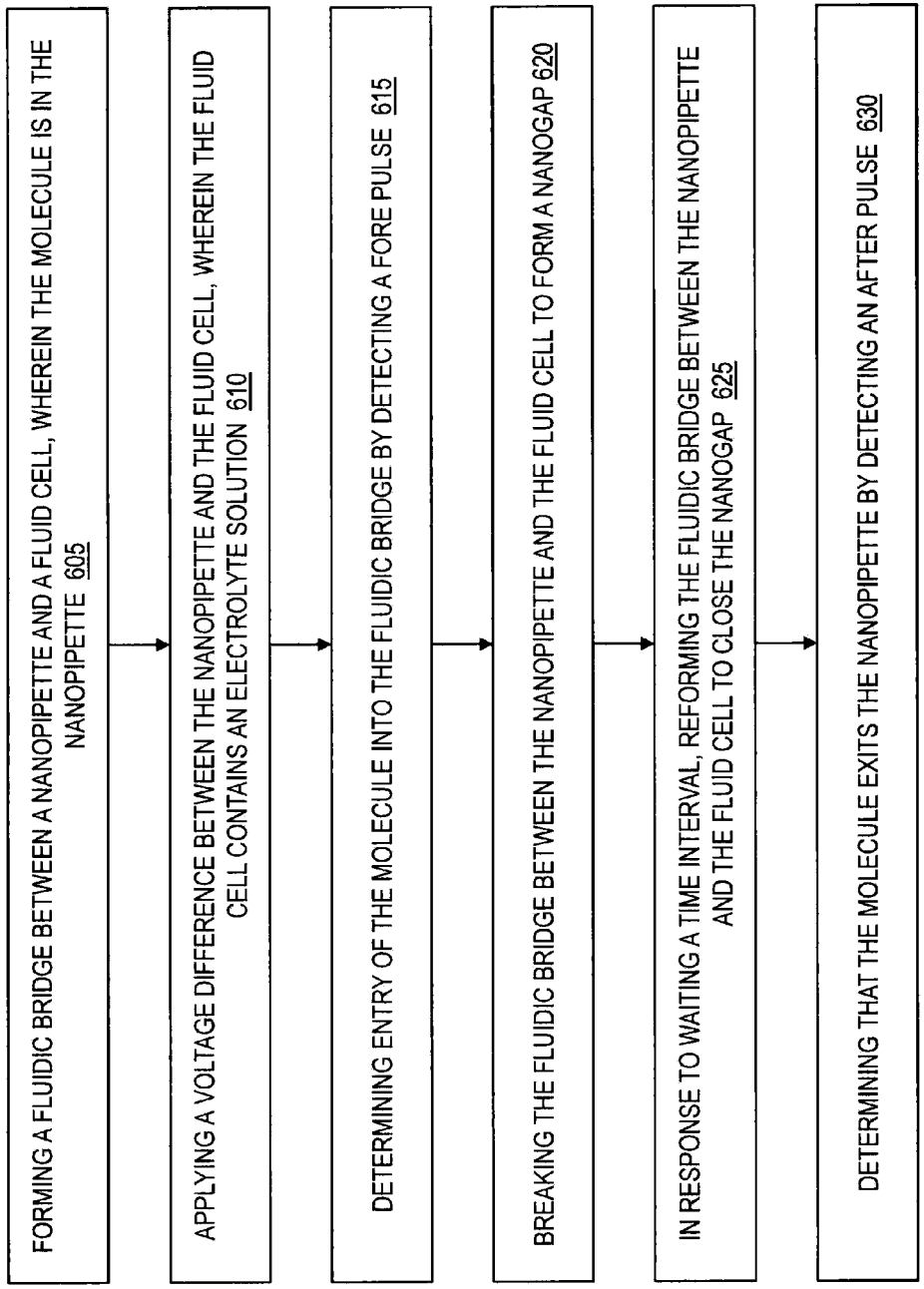
FIG. 6 is a flow chart of a method for electrical detection of a molecule according to an embodiment.

FIG. 6 is a flow chart 600 of a method for electrical detection of a molecule 10 according to an embodiment. The various operations in FIG. 6 may be controlled by, initiated by, and/or caused by the control system 30 (which may be implemented in the computer 800). The control system 30 may include memory to receive/store triggers, receive/store ionic current measurements (current spikes/pulses), and store computer executable instructions for operating the test setup 100 as discussed herein.

At block 605, the z stage 25 nanopositioner (via control system 30) forms the fluidic bridge 260 between the nanopipette 45 and the fluid cell 20, where the molecule 10 is in the nanopipette 45.

At block 610, the voltage source 40 applies (via control system 30) a voltage difference (voltage bias) between the nanopipette 45 and the fluid cell 20, where the fluid cell 20 and the nanopipette 45 both contain the electrolyte solution 15. The fluidic bridge 260 is the fluid connection of the electrolyte solution 15 in both the fluid cell 20 and the nanopipette 45 such that an electrical connection (circuit) is formed to conduct electricity (ionic current), when the voltage is applied.

At block 615, the control system 30 determines entry of the molecule 10 into the fluidic bridge 260 (and into the fluidic cell 20) by detecting the fore pulse 205.

At block 620, the control system 30 instructs the z stage 25 nanopositioner to move upward for breaking the fluidic bridge 260 between the nanopipette 45 and the fluid cell 20 in order to form the nanogap 250.

In response to waiting a time interval (e.g., predetermined amount of milliseconds (ms)), the control system 30 is configured to reform the fluidic bridge 260 between the nanopipette 45 and the fluid cell 20 to close the nanogap 250 at block 625.

At block 630, the control system 30 is configured to determine that the molecule 10 exits the nanopipette 45 by detecting the after pulse 215.

Forming the fluidic bridge between the nanopipette and the fluid cell comprises bringing the tip 220 of the nanopipette 45 into physical contact with the electrolyte solution 15 in the fluid cell 20, thereby creating the fluidic bridge 260. The voltage difference (e.g., $V_b$ applied by the voltage source 40) drives the molecule 10 to begin exiting the nanopipette 45 and entering the electrolyte solution 15 in the fluid cell 20.

Breaking the fluidic bridge 260 between the nanopipette 45 and the fluid cell 20 to form the nanogap 250 comprises moving the tip 220 of the nanopipette 45 a distance away from the electrolyte solution 15 (in the fluid cell 20) such that a first part 405 of the molecule 10 is in the electrolyte solution 15 and a second part of the molecule remains in the nanopipette. Strictly speaking, the second part is actually the last part 415 in FIG. 4 since the middle/second part 410 is in the nanogap 250.

In response to breaking the fluidic bridge trapping the molecule between the nanopipette and the fluid cell, the control system 30 is configured to cause the trapping of the molecule by having a first part 405 of the molecule in the electrolyte solution 15 and a second part (which is the last part 415 in FIG. 4) of the molecule in the nanopipette 45. The molecule 10 is trapped so as to extend through the nanogap 250 as shown in FIGS. 2 and 4.

A first coating molecule 450_A is attached to the first part 405 of the molecule 10. The first coating molecule 450_A is trapped at a surface-to-fluid interface of the electrolyte solution 15 (i.e., the surface 60) when the nanogap 250 is formed, thereby trapping the first part 405 of the molecule at the surface-to-fluid interface as shown FIG. 4B.

A second coating molecule 450_B is attached to the second part of the molecule (which is shown as the last part 415). The second coating molecule 450_B is trapped in the tip 220 of the nanopipette 45 when the nanogap 250 is formed, thereby trapping the second part of the molecule in the tip of the nanopipette. The control system 30 is configured to cause the z stage 25 of the nanopositioner to stretching the middle part 410 of the molecule 10 extended through the nanogap 250 by moving the nanopipette away from the fluid cell 20.

The fore pulse 205 is a spike in ionic current that indicates translocation of the molecule through the tip of the nanopipette 45 (as shown in stage A in FIG. 2). The fore pulse 205 is a trigger (received by the control system 30) for the nanopipette 45 to be moved away from the fluid cell 20, thus creating the nanogap 250. The after pulse 215 is another spike in the ionic current indicating (to the control system 30) that the molecule 10 has completely exited the tip of the nanopipette.

Further information of the control system 30 is discussed below. To discuss an example of the control system 30, the control system 30 may be an embedded controller by National Instruments (NI, Austin, Tex.) PXI-8108, located inside NI PXI-1031 chassis, which runs LabView graphical user interface (GUI) and data logging service. The control system 30 may have an NI PXI-7852R board, located inside the same chassis, which features an FPGA chip and several 16-bit 1 MHz analog input/output channels. There may be a Synchronous Finite State Machine (FSM), specified with LabView's State Chart diagrams, running on the FPGA at a frequency of 0.2 MHz, in order to operate as discussed herein.

As noted above, the control system 30 (which may include and/or be implemented in the computer system 800) is configured to perform a series of actions. In particular, detection of the fore pulse 205 triggers the sequence of actions by the control system 30, including raising the pipette tip position $Z_p$ (assuming that the tip position starts in physical contact (which may include dipping the tip 220 into the electrolyte solution 15 in the fluidic cell 20) with the surface 60 so as to form the fluidic bridge 260) and changing (via voltage source 40) the bias voltage ($V_b$) while measuring the pipette current $I_p$ via meter 35. The actions and their duration are programmable in the control system 30 as understood by one skilled in the art.

Figure 7:
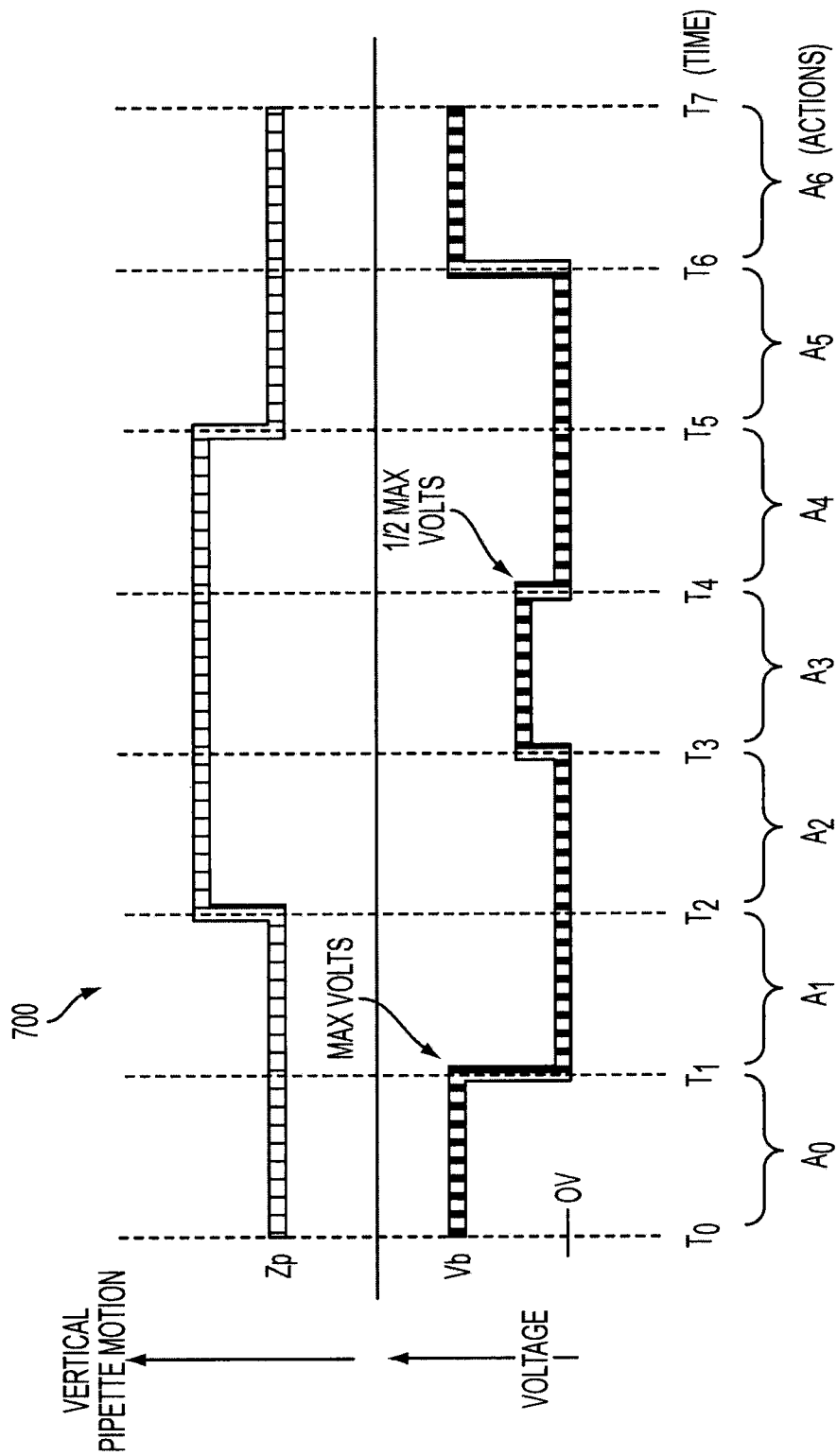
FIG. 7 illustrates a graph of example sequence of actions performed/caused by the according to an embodiment.

FIG. 7 is a graph 700 illustrating example sequence of actions performed by the control system 30 according to an embodiment. The x-axis shows the time and corresponding actions. The y-axis shows the voltage bias ($V_b$) applied at each time and for each action. Also, the y-axis shows the vertical positioning waveform ($Z_p$) of the nanopipette 45 (tip) during each time and for each action. The vertical positioning waveform $Z_p$ denotes the position of the nanopipette 45 for each bias voltage ($V_b$). Time $t_0$ through $t_7$ corresponds to action start times, and labels A0 through A6 name the actions.

While the voltage bias ($V_b$) is being applied and after detecting a fore pulse at $t_0$, the control system 30 passively monitors ionic current $I_p$ without changing any controls (action 0 (A0)). Duration $t_1$-$t_0$ of A0 is selected in such a way as to allow the charged molecule 10 to translocate partially into the fluidic cell 20 (as shown in stage A in FIG. 2). For example, the duration $t_1$-$t_0$ may be 2-5 ms. At $t_1$ action A1 drops the bias voltage ($V_b$) to zero, removing the drift component of translocation, and leaving only the Brownian diffusion of the charged molecule 10. Soon after, at $t_2$ A2 raises the tip 220 and opens the nanogap 250 between the liquid surface 60 and the nanopipette tip 220. This traps and/or stretches the molecule 10 in the nanogap 250. Actions A3 and A4 allow the probing of the molecule 10 stretched in the nanogap 250 by changing $V_b$ and the monitoring $I_p$. In one case, a non-zero $V_b$ is applied during A3 which allows the control system 30 to detect a current through the molecule 10 stretched in the nanogap 250. In another case, the $V_b$ is set to 0 V when the molecule 10 is stretched at time A3 and A4. Also, the stretched part 410 of the molecule 410 may be placed under a microscope (not shown). Fluorescent markers may have been applied to the molecule in advance for viewing it under an optical microscope. At time $t_5$, the pipette tip 220 closes the nanogap 250 by lowering $Z_p$ (action A5), and after a short delay (e.g., 2-5 ms), needed to separate the effects of $Z_p$ and $V_b$ changes on $I_p$, the bias voltage ($V_b$) is restored at $t_6$. At this moment of $t_6$ (action A6), the after pulse 215 can be observed, corresponding to the molecule 10 having been in the tip 220 and is now just exiting the tip 220. Time $t_7$ corresponds to re-starting the process (sequence of actions) over again just as depicted for time $t_0$.

Figure 8:
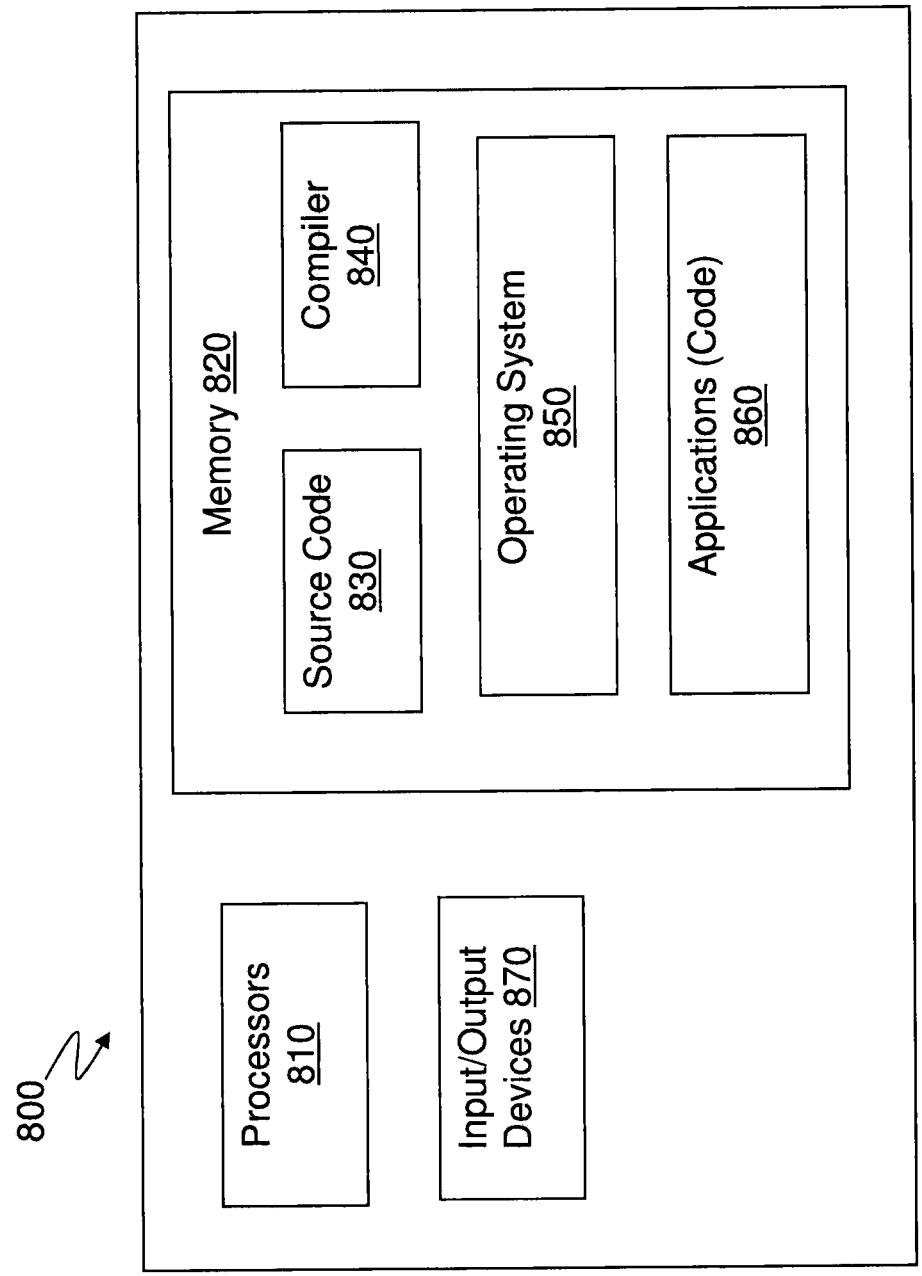
FIG. 8 illustrates a computer test setup which may implement, control, and/or regulate features discussed herein according to an embodiment.

Now turning to FIG. 8, FIG. 8 illustrates an example of a computer system 800 (e.g., as part of the computer test setup for testing and analysis) which may implement, control, and/or regulate the respective voltages of the voltage sources, respective measurements of ammeters, and display screens for displaying various current amplitude as would be understood to one skilled in the art. The computer system 800 may store results, time stamps, readings, applied voltages, measurements, etc., taken during the testing and analysis.

Various methods, procedures, modules, flow diagrams, tools, applications, circuits, elements, and techniques discussed herein may also incorporate and/or utilize the capabilities of the computer 800. Moreover, capabilities of the computer 800 may be utilized to implement features of exemplary embodiments discussed herein. One or more of the capabilities of the computer 800 may be utilized to implement, to connect to, and/or to support any element discussed herein (as understood by one skilled in the art. For example, the computer 800 which may be any type of computing device and/or test equipment (including ammeters, voltage sources, current meters, connectors, etc.). Input/output device 870 (having proper software and hardware) of computer 800 may include and/or be coupled to the nanodevices and structures discussed herein via cables, plugs, wires, electrodes, patch clamps, pads, etc. Also, the communication interface of the input/output devices 870 comprises hardware and software for communicating with, operatively connecting to, reading, and/or controlling voltage sources, ammeters, and current traces (e.g., magnitude and time duration of current), etc., as understood by one skilled in the art. The user interfaces of the input/output device 870 may include, e.g., a track ball, mouse, pointing device, keyboard, touch screen, etc., for interacting with the computer 800, such as inputting information, making selections, independently controlling different voltages sources, and/or displaying, viewing and recording current traces for each base, molecule, macromolecules, biomolecules, etc.

Generally, in terms of hardware architecture, the computer 800 may include one or more processors 810, computer readable storage memory 820, and one or more input and/or output (I/O) devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a data signal processor (DSP), or an auxiliary processor among several processors associated with the computer 800, and the processor 810 may be a semiconductor based microprocessor (in the form of a microchip) or a macroprocessor.

The computer readable memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the computer readable memory 820 may include one or more separate programs, each of which comprises an ordered listing of executable instructions for implementing logical functions. The software in the memory 820 includes a suitable operating system (O/S) 850, compiler 840, source code 830, and one or more applications 860 of the exemplary embodiments. As illustrated, the application 860 comprises numerous functional components for implementing the features, processes, methods, functions, and operations of the exemplary embodiments.

The operating system 850 may control the execution of other computer programs, and provides scheduling, input-output control, file and data management, memory management, and communication control and related services.

The application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as (a) an object oriented programming language, which has classes of data and methods, or (b) a procedure programming language, which has routines, subroutines, and/or functions.

The I/O devices 870 may include input devices (or peripherals) such as, for example but not limited to, a mouse, keyboard, scanner, microphone, camera, etc. Furthermore, the I/O devices 870 may also include output devices (or peripherals), for example but not limited to, a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or an intranet. The I/O devices 870 may be connected to and/or communicate with the processor 810 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 860 is implemented in hardware, the application 860 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for electrical detection of a molecule, the method comprising:

dipping a tip of a nanopipette into an electrolyte solution in a fluid cell, in order to form a fluidic bridge between the nanopipette and the electrolyte solution in the fluid cell, wherein the molecule is in the nanopipette;

applying a voltage difference between the nanopipette and the fluid cell, wherein the fluid cell contains the electrolyte solution;

determining entry of the molecule into the fluidic bridge by detecting a fore pulse;

breaking the fluidic bridge between the nanopipette and the electrolyte solution in the fluid cell to form a nanogap by moving the nanopipette away from the fluid cell such that a middle portion of the molecule is in the nanogap, wherein no electrolyte solution is in the nanogap, wherein the fluidic cell is a container having an open top, wherein the nanopipette is positioned vertically above the open top of the fluidic cell to create the nanogap, wherein a nanopipette width of the nanopipette is less than a width of the open top of the fluidic cell;

recognizing that the nanogap is created by detecting a pulse break, no ionic current being detected for the pulse break;

in response to waiting a time interval, reforming the fluidic bridge between the nanopipette and the electrolyte solution in the fluid cell to close the nanogap; and determining that the molecule completely exits the nanopipette to reside in the fluid cell by detecting an after pulse.

2. The method of claim 1, wherein forming the fluidic bridge between the nanopipette and the electrolyte solution in the fluid cell comprises bringing a tip of the nanopipette into physical contact with the electrolyte solution in the fluid cell, thereby creating the fluidic bridge;

wherein the voltage difference drives the molecule to begin exiting the nanopipette and entering the electrolyte solution in the fluid cell.

3. The method of claim 1, wherein breaking the fluidic bridge between the nanopipette and the fluid cell to form the nanogap comprises moving a tip of the nanopipette a distance away from the electrolyte solution such that a first part of the molecule is in the electrolyte solution and a second part of the molecule remains in the nanopipette.

4. The method of claim 1, further comprising in response to breaking the fluidic bridge trapping the molecule between the nanopipette and the fluid cell, trapping the molecule by having a first part of the molecule in the electrolyte solution and a second part of the molecule in the nanopipette.

5. The method of claim 4, wherein the molecule is trapped so as to extend through the nanogap.

6. The method of claim 4, wherein a first coating is attached to the first part of the molecule;

wherein the first coating is trapped at a surface-to-fluid interface of the electrolyte solution when the nanogap is formed, thereby trapping the first part of the molecule at the surface-to-fluid interface.

7. The method of claim 6, wherein a second coating is attached to the second part of the molecule;

wherein the second coating is trapped in a tip of the nanopipette when the nanogap is formed, thereby trapping the second part of the molecule in the tip of the nanopipette.

8. The method of claim 7, further comprising stretching a middle part of the molecule extended through the nanogap by moving the nanopipette away from the fluid cell.

9. The method of claim 1, wherein the fore pulse is a spike in ionic current that indicates translocation of the molecule through a tip of the nanopipette;

wherein the fore pulse is a trigger for the nanopipette to be moved away from the fluid cell to thus create the nanogap.

10. The method of claim 9, wherein the after pulse is another spike in the ionic current indicating that the molecule has completely exited the tip of the nanopipette.

11. A method for electrical detection of binding of a protein to a molecule, the method comprising:

dipping a tip of a nanopipette into an electrolyte solution in a fluid cell, in order to form a fluidic bridge between the nanopipette and the electrolyte solution in the fluid cell, wherein the molecule and the protein are in the nanopipette;

applying a voltage difference between the nanopipette and the fluid cell, wherein the fluid cell contains an electrolyte solution;

determining entry of the molecule into the fluidic bridge by detecting a fore pulse;

breaking the fluidic bridge between the nanopipette and the electrolyte solution in the fluid cell to form a nanogap by moving the nanopipette away from the fluid cell such that a middle portion of the molecule is in the nanogap, wherein no electrolyte solution is in the nanogap, wherein no electrolyte solution is in the nanogap, wherein the fluidic cell is a container having an open top, wherein the nanopipette is positioned vertically above the open top of the fluidic cell to create the nanogap, wherein a nanopipette width of the nanopipette is less than a width of the open top of the fluidic cell;

recognizing that the nanogap is created by detecting a pulse break, no ionic current being detected for the pulse break;

in response to waiting a time interval, reforming the fluidic bridge between the nanopipette and the electrolyte solution in the fluid cell to close the nanogap; and determining that the protein is bound to the molecule by detecting an after pulse when the molecule completely exits the nanopipette to reside in the fluid cell.

12. The method of claim 11, wherein the molecule is a DNA molecule.

13. The method of claim 11, further comprising determining that the protein is not bound to the molecule by at least one of:

detecting no after pulse after the nanogap has been closed to reform the fluidic bridge; and detecting the after pulse with a baseline magnitude corresponding to the molecule being unbound, the baseline magnitude is lower than a magnitude corresponding to the protein being bound to the molecule.

* * * * *